United States Patent [19]

Carver

[11] Patent Number: 4,825,169
[45] Date of Patent: Apr. 25, 1989

[54] ULTRASONIC STREAMING CURRENT DETECTOR

[75] Inventor: John F. Carver, Jupiter, Fla.

[73] Assignee: Milton Roy Company, St. Petersburg, Fla.

[21] Appl. No.: 71,297

[22] Filed: Jul. 9, 1987

[51] Int. Cl.$^4$ .............................................. G01N 27/60
[52] U.S. Cl. .................................. 324/453; 324/71.1; 324/447; 134/1
[58] Field of Search ...................... 324/453, 71.1, 175, 324/438, 439, 444, 446, 447, 450, 452; 134/1, 143, 184; 204/193, 280

[56] References Cited

U.S. PATENT DOCUMENTS

| | | | |
|---|---|---|---|
| 3,368,144 | 2/1968 | Gerdes | 324/453 |
| 3,368,145 | 2/1968 | Gerdes | 324/453 |
| 3,369,984 | 2/1968 | Gerdes et al. | 324/71.1 X |
| 3,399,133 | 8/1968 | Gerdes et al. | 324/453 |
| 3,746,988 | 7/1973 | Ford et al. | 324/175 |
| 4,297,640 | 10/1981 | Moore | 324/458 |
| 4,446,435 | 4/1984 | Canzoneri | 324/71.1 X |

*Primary Examiner*—Reinhard J. Eisenzopf
*Assistant Examiner*—Robert W. Mueller
*Attorney, Agent, or Firm*—Woodcock Washburn Kurtz Mackiewicz & Norris

[57] ABSTRACT

A streaming current detector includes an optical shutter rotated by the shaft of the motor which reciprocates a piston between electrodes in a bore containing sample fluid. An electronic synchronous detector is controlled by the output of a light detector whose source is interrupted by the optical shutter. The alternating current signals from the electrodes are connected to an operational amplifier having its inverting input connected to its output solely by a capacitor so that the output voltage is proportional to the charge of the fluid.

7 Claims, 1 Drawing Sheet

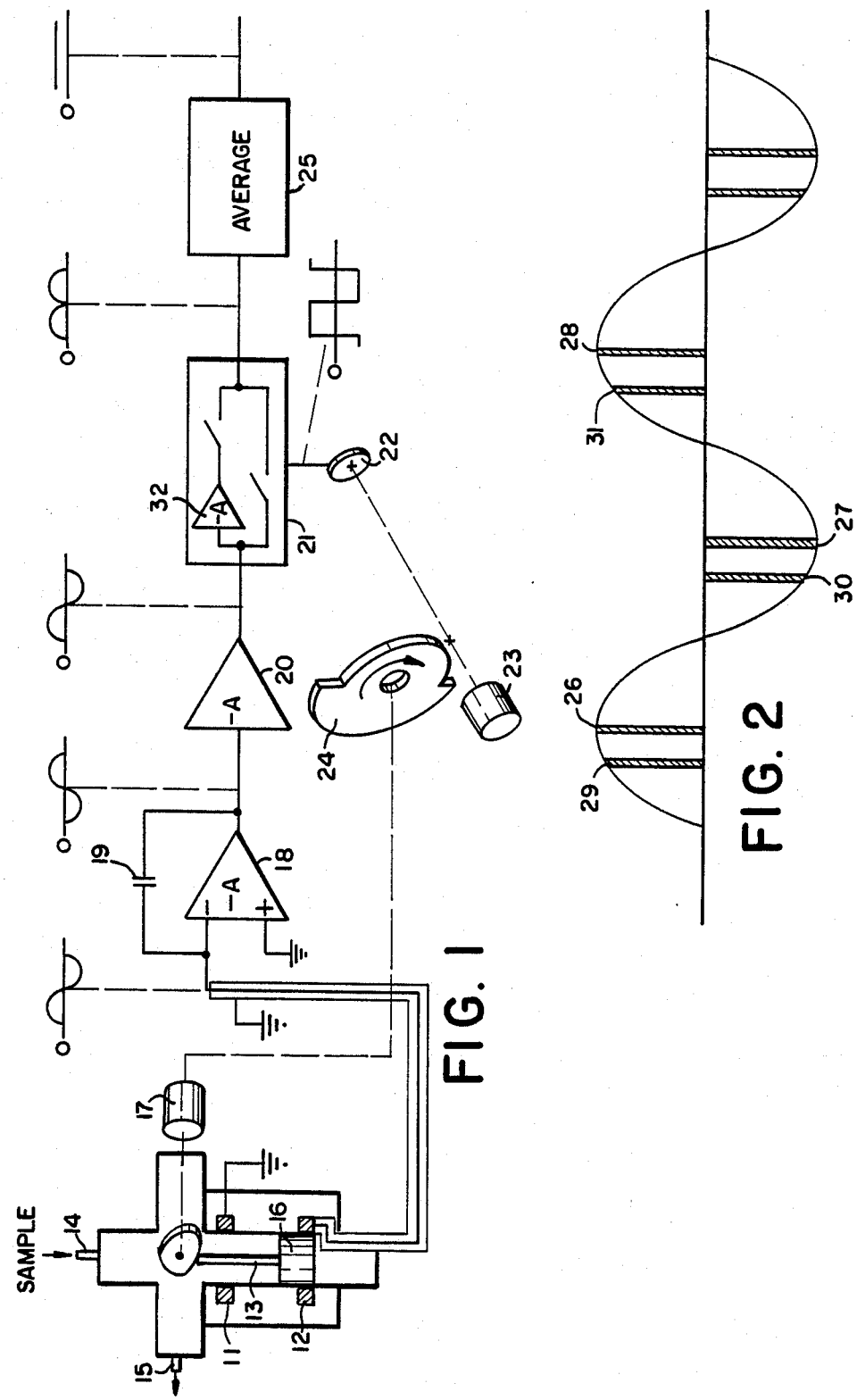

ULTRASONIC STREAMING CURRENT DETECTOR

BACKGROUND OF THE INVENTION

1. Field of the Invention

The present invention relates to an improved apparatus for determining the charge of aqueous suspensions of finely divided, solid, charged particles.

2. General Background

Coagulation and flocculation are frequently employed to clarify aqueous solutions containing suspended particles. Once coagulated and flocculated, the suspended particles can be separated from their fluid medium by sedimentation, filtration, flotation, or centrifugation. Coagulation is promoted by the use of chemicals such as alum, ferric chloride or various polymeric materials such as water-soluble cationic and anionic organic polyelectrolytes. The polymeric materials are also used as flocculents. Flocculation is used for example, in a paper machine head box within a paper manufacturing process operation and in many other contexts.

U.S. Pat. Nos. 3,368,144 and 3,368,145-Gerdes describe a detector which develops a signal which can be used in the continuous regulaton of flocculation of aqueous suspensions of finely divided charged particles and for other uses, such as detecting electrical charges present in a stream having ions, charged molecules, or colloidal particles therein. In the Gerdes apparatus, a magnetically actuated mechanical switch is used to synchronously detect the alternating current signal developed between two electrodes as a piston moves a fluid sample containing charged particles past the electrodes in periodically alternating directions.

U.S. Pat. Nos. 3,369,984, 3,399,133 and 3,526,827 also describe prior art detectors.

U.S. Pat. No. 4,446,435-Canzoneri, describes an improvement on the streaming current detector of the Gerdes patent. As noted in column 6, line 45 et seq. of the Canzoneri patent, the mechanical switch used in the prior art to commutate the alternating current signal, was a common cause of failure. As shown in the Canzoneri patent, the mechanical switch was eliminated and replaced by an optical isolator. The optical isolator of Canzoneri consisted of a light emitting diode source and photodiode light detector. The light emitting diode source generated and directed a beam of light onto the reflective surface of a rotating disk and the photodiode detector sensed the presence of the reflected light. A non-reflective mark on the disk periodically interrupted the beam of reflected light from the disk which was sensed by the photodiode detector. The resultant photodetector output signal was synchronized with the stroke of the piston and was used to control the periodic sampling of the voltage from the electrodes.

Problems have been encountered in the use of reflective optical isolator devices of the type shown in Canzoneri. One problem is their inherent sensitivity to stray light and marginally reflective surfaces. These two characteristics can cause erroneous output signals resulting in incorrect signal detection.

Another problem encountered in prior art streaming current detectors is that the amplifier for the electrodes is sensitive to sample fluid parameters other than charge and does not accurately measure the charge condition of the fluid under all conditions. In addition, prior art streaming current detector amplifiers are sensitive to input cable capacitance making system calibration and repair difficult to accomplish.

It is an object of the present invention to provide an improved streaming current detector which obviates these and other problems.

SUMMARY OF THE INVENTION

In accordance with the present invention, an ultrasonic streaming current detector includes an electronic synchronous detector which is operated by an optical shutter, so that fully synchronous detection is obtained over the full cycle of the alternating current signal developed by the electrodes.

An alternating electrical signal which is responsive to the charge or electric potential contained by the streaming sample fluids is generated at the electrodes. This signal is transmitted through a coaxial cable to the input of a charge amplifier. The resulting output signal is further amplified and directed to the analog input port of the electronic full wave synchronous detector for processing. An optical system consisting of a light source, light detector and optical shutter are located near the piston drive motor. This system monitors the position of the reciprocating piston and generates a signal which represents the direction of travel of the piston as a function of time. This piston "phase" signal is directed to the phase control input port of the synchronous detector. The detector processes the analog input signal as a function of piston travel direction producing a direct current output signal proportional in amplitude and polarity to the charge or electric potential contained in the fluid samples at the electrodes. The detector output signal is directed to an averaging circuit which makes it suitable for measurement and control devices such as meters, alarm indicators, relays and process control signal converters.

Unlike other systems using magnets or reflective devices, the present invention employs an optical shutter to facilitate mechanical interruption of a light path transmitted between a closely coupled infrared LED source and a photodiode detector The shutter mechanism is attached to the piston drive motor shaft and its profile is designed to permit transmission of light during 180 degrees of shutter rotation and interrupt the light path during the following 180 degrees of shutter rotation. In this configuration, the photodiode detector provides a square wave electrical output signal that is directly related to the direction of travel (phase) of the piston. It is important to note that this configuration provides piston travel direction information during the full 360 degrees of motor rotation. Because this position sensor configuration relies on the direct transmission of a closely coupled infrared LED light source and sensor it is insensitive to stray light from direct and reflected sources.

In accordance with another aspect of the invention, the operational amplifier used to process the charge signal from the electrodes is configured to function as a charge amplifier (Q-Amp). The changes in electrical charge picked up by the electrodes are directed to the Q-Amp where they are converted to an analog output voltage. This Q-Amp is inherently insensitive to a wide range of fixed input electrical capacitance thus permitting the use of varying lengths of the coaxial cable connecting the electrodes to the charge amplifier. This permits separation of the electrodes from the electronics by several hundred feet if desired, and was not possible in previous art. Furthermore, changes in input coaxial cable length do not require recalibration of the instrument. The Q-Amp also minimizes the pickup and amplification of stray electrical noise signals.

The foregoing and other objects, features and advantages of the invention will be better understood from the following more detailed and appended claims.

SHORT DESCRIPTION OF THE DRAWINGS

FIG. 1 shows the invention in schematic form and includes the waveforms of electrical signals; and FIG. 2 depicts detecting problems with the prior art.

DESCRIPTION OF THE PREFERRED EMBODIMENT

Referring to FIG. 1, a pair of electrodes 11 and 12 are disposed in a bore 13. Sample fluid flows through inlet 14 and outlet 15. A loosely fit piston 16 reciprocates in the bore between electrodes 11 and 12, thereby pushing sample fluid past the electrodes first in one direction and then in the other direction.

A motor 17 has a shaft connected to a cam or the like which reciprocates the piston 16 in the bore.

Electrodes 11 and 12 are connected through coaxial cable to the amplifying circuitry which includes operational amplifier 18. Operational amplifier 18 has an inverting input which is coupled to its output solely by the capacitor 19. In this configuration, the operational amplifier 18 produces a voltage which is directly proportional to the charge of the sample fluid. Operational amplifier 18 produces an output given by:

$$Q = CE$$

where
  Q is the charge of the fluid;
  C is the capacitance of capacitor 19; and
  E is the output voltage.

The output of operational amplifier 18 is further amplified in amplifier 20, the output of which is applied to the input port of electronic synchronous detector 21. In one actual embodiment of the invention, the output signal from amplifier 20 is directed to both the inverting and non-inverting inputs of an operational amplifier 32 which is configured for unity gain. Electronic switches consisting of field effect transistors are appropriately connected to the operational amplifier 32 providing a control-port through which the selection of inverting or non-inverting amplification can be made by remote electrical signals.

The control port of synchronous detector 21 is connected to the output of light detector 22. Light detector 22 and light source 23 are on opposite sides of a rotating optical shutter 24. Shutter 24 is a disk shaped element, having a portion which is cut away to pass light between source 23 and detector 22. The remaining portion of shutter 24 blocks light between source 23 and detector 22. Shutter 24 is rotated by the shaft of motor 17 and is in synchronism with the reciprocation of piston 16. Shutter 24 blocks light from source 23 and detector 22 during the portion of its rotation in which the piston is reciprocating in one direction and passes light from source 23 to detector 22 during the portion of its rotation in which piston 16 is moving in the other direction. Although the shutter 24 is depicted as disk with a portion of its circumference removed to permit light transmission, the shutter could also be configured as a disk of fixed diameter in which half of its area, as divided at the diameter, is transparent and the remaining half is opaque. The latter configuration is much safer should a user or service technician accidentally touch the rotating disk.

Light detector 22 produces an electrical output signal indicating the direction of travel of the piston. This output controls synchronous detector 21 to produce full wave detection of the output of amplifier 20 in synchronism with the direction of reciprocation of the piston. The output of synchronous detector 21 is applied to an averaging circuit 25 which produces an output proportional to the charge of the sample fluid.

Operation of the synchronous detector 21 can be better understood by observing the waveforms of the electrical signals depicted in FIG. 1. The square wave output signal f, from photodetector 22 is utilized to select inverting or non-inverting amplification by the synchronous detector 21. Amplified electrode charge signal c, is input to the synchronous detector 21 where inverting or non-inverting amplification occurs, depending on the amplitude and phase of control signal f. The resulting output signal is depicted in d. Averaging circuit 25 processes this signal to a form shown in e.

FIG. 2 depicts the alternating current signal produced by the electrodes. In the prior art, such as that disclosed in the Canzoneri patent, detection of this alternating current signal occurs during sample intervals such as at 26 and 28. However, because fluid sample parameters other than electrical charge can affect the electrode amplifier, the sample intervals can change with respect to time and are depicted as 29 and 31. Only a small fraction of the entire electrical signal period is sampled; therefore, small changes in sample intervals 32 can readily produce output signal amplitude variations 30 which are not truly representative of the charge of the sample fluid. In addition, the measurement of small sample charges is precluded by the small signal-to-noise ratios inherent in the prior art.

These problems are obviated by the present invention by utilizing a charge amplifier to process the electrode signals and by synchronously detecting the alternating current signal of the electrodes over the full 2 pi radians of the alternating current signal.

While a particular embodiment of the invention has been shown and described, various modifications are within the true spirit and scope of the invention. The appended claims are, therefore, intended to cover all such modifications.

What is claimed is:

1. A streaming current detector for determining the charge condition in a fluid comprising:
   a pair of electrodes disposed in a bore;
   a reciprocating piston disposed in said bore;
   means for reciprocating said piston;
   a light shutter operated by said last named means;
   a light source and a light detector on opposite sides of said shutter, said shutter passing light from said source to said detector while said piston is reciprocating in one direction, and blocking light from said source to said detector while said piston is reciprocating in the other direction, said light detector producing an output indicating the direction of travel of said piston;
   an electronic synchronous detector controlled by said output of said light detector; and
   an amplifier for amplifying electrical signals generated across said electrodes, the output of said amplifier being connected to said synchronous detector to produce full wave detection of the output of said amplifier in synchronism with the direction of reciprocation of said piston.

2. The detector recited in claim 1 wherein said means for reciprocating said piston comprises:
   a motor having a shaft connected to means to reciprocate said piston.

3. The detector recited in claim 2 wherein said shutter is rotated by said shaft, said shutter passing light from said source to said detector during the portion of its rotation in which said piston is reciprocating in one direction, and blocking light from said source to said detector during the portion of its rotation in which said piston is reciprocating in the other direction.

4. The detector recited in claim 3 wherein said shutter is a disk shaped element with a portion of the disk cut away to pass light from said source to said detector and the remaining portion of said disk blocks said light.

5. The detector recited in claim 3 wherein said shutter is a disk shaped element of constant diameter in which a portion of the disk is transparent and the remaining portion is opaque.

6. The detector recited in claim 1 wherein said amplifier is an operational amplifier having an inverting input coupled to its output solely by a capacitance, so that the output voltage of said operational amplifier is proportional to the charge of said fluid.

7. The detector recited in claim 1 further comprising:
   an averaging circuit, the output of said synchronous detector being connected to said averaging circuit which produces an output voltage proportional to the charge of said fluid.

* * * * *